United States Patent [19]

Albonetti et al.

[11] Patent Number: 6,083,869
[45] Date of Patent: Jul. 4, 2000

[54] METHOD FOR PREPARING AMMOXIDATION CATALYSTS

[75] Inventors: Stefania Albonetti, Imola, Italy; Gilbert Blanchard, Le Plessis-Belleville; Paolo Burattin, Lyons, both of France; Fabrizio Cavani, Modena; Ferruccio Trifiro, Bologna, both of Italy

[73] Assignee: Rhodia Fiber and Resin Intermediates, Courbevoie Cedex, France

[21] Appl. No.: 09/043,648

[22] PCT Filed: Sep. 27, 1996

[86] PCT No.: PCT/FR96/01510

§ 371 Date: Jun. 11, 1998

§ 102(e) Date: Jun. 11, 1998

[87] PCT Pub. No.: WO97/12839

PCT Pub. Date: Apr. 10, 1997

[30] Foreign Application Priority Data

Sep. 29, 1995 [FR] France ................... 95 11680

[51] Int. Cl.$^7$ .................. B01J 23/00; B01J 23/745; C07C 253/00
[52] U.S. Cl. .......... 502/325; 502/338; 502/353; 558/318; 558/319; 558/320; 558/325
[58] Field of Search ................... 502/325, 338, 502/353; 558/318, 319, 320, 325

[56] References Cited

U.S. PATENT DOCUMENTS

| | | | |
|---|---|---|---|
| 4,060,500 | 11/1977 | Clavenna | 252/471 |
| 4,257,921 | 3/1981 | Slinkard | 252/462 |
| 4,769,355 | 9/1988 | Glaeser et al. | 502/312 |
| 4,801,727 | 1/1989 | Glaeser et al. | 558/319 |
| 5,008,427 | 4/1991 | Brazdil | 558/319 |
| 5,214,016 | 5/1993 | Brazdil et al. | 502/202 |
| 5,332,855 | 7/1994 | Blanchard et al. | 558/319 |
| 5,686,381 | 11/1997 | Albonetti et al. | 502/353 |

FOREIGN PATENT DOCUMENTS

| | | |
|---|---|---|
| 0 306 973 | 3/1989 | European Pat. Off. . |
| 0 455 529 | 10/1991 | European Pat. Off. . |
| 0 558 424 | 9/1993 | European Pat. Off. . |

*Primary Examiner*—Mark L. Bell
*Assistant Examiner*—Patricia L. Hailey
*Attorney, Agent, or Firm*—Burns, Doane, Swecker & Mathis, L.L.P.

[57] ABSTRACT

The present invention relates to a process for the preparation of mixed vanadium, antimony and iron oxides and to their use as catalysts for the ammoxidation of alkanes. The process for the preparation of a mixed oxide defined above is characterized in that:

respective vanadium, antimony and iron compounds are dissolved in at least one saturated alcohol or in water, the alcoholic solution or the aqueous solution thus obtained is brought into contact with an aqueous solution containing an ammonium salt, in order to precipitate the mixed oxide, the mixed oxide obtained is separated and calcined.

27 Claims, No Drawings

METHOD FOR PREPARING AMMOXIDATION CATALYSTS

The present invention relates to a new process for the preparation of mixed vanadium, antimony and iron oxides and to the use of these oxides as catalysts for the ammoxidation of alkanes.

Certain mixed oxides of vanadium and of antimony or of vanadium, of antimony and of other metals are known compounds which have been described, among many other mixed oxides, in Patent FR-A-2, 072,334.

A description is given, in U.S. Pat. No. 5,008,427, of a process for the ammoxidation of propane or of butane in the presence of a catalyst which can comprise, in particular, oxides of vanadium, of antimony and of iron or of titanium or of chromium or of gallium or of tin, and optionally of other metals. These catalysts exhibit the essential characteristic of having been calcined at a temperature equal to or greater than 780° C.

A description has likewise been given, in Patent EP-A-0,558,424, of a process for the ammoxidation of alkanes which is catalysed by mixed oxides of vanadium, of antimony, of iron and/or of gallium and/or of indium. These mixed oxides are prepared by mixing aqueous suspensions of compounds of the various metals, heating with stirring and then evaporating the water, drying and calcining.

The present invention relates to a new process for the preparation of a mixed vanadium, antimony and iron oxide corresponding to the general empirical formula (I):

$$VSb_aFe_bO_x \qquad (I)$$

in which:
a represents a whole or fractional number equal to or greater than 0.1
b represents a whole or fractional number equal to or greater than 0.5
x represents a whole or fractional number determined by the oxidation state of the other elements,
characterized in that:
respective vanadium, antimony and iron compounds are dissolved in at least one saturated alcohol or in water,
the alcoholic solution or the aqueous solution thus obtained is brought into contact with an aqueous solution containing an ammonium salt, in order to precipitate the mixed oxide,
the mixed oxide obtained is separated and calcined.

The vanadium, antimony and iron compounds used in the process must be soluble in a saturated alcohol or a mixture of saturated alcohols or in water.

In the present text, a compound is regarded as soluble when its solubility, measured at 25° C., is at least 5 grams per liter of saturated alcohol or of water. These compounds can be introduced together; they can also, first of all, be dissolved separately in an alcohol, the various alcoholic solutions thus obtained then being mixed with each other. They can also, first of all, be dissolved separately in water, the various aqueous solutions thus obtained then being mixed with each other. Generally, but non-limitingly, an alcoholic solution or an aqueous solution is prepared by dissolving the various compounds, without intermediate preparation of solutions of each of the vanadium, antimony and iron compounds.

To prevent the decomposition or the precipitation of certain compounds, more particularly of the iron salts, it is preferable to use an acidic aqueous solution having a pH of less than or equal to 2, when the catalysts of the invention are prepared in water.

In this case, the acid used to prepare this acidic aqueous solution can be any strong inorganic or organic acid capable of giving a solution having a pH of less than or equal to 2 and preferably a pH of 0.5 to 1.

Mention may be made, as non-limiting examples of such acids, of, in particular, hydrochloric, hydrobromic, sulphuric, nitric and trifluoroacetic acids.

For convenience, it is preferable to use the acid corresponding to the iron salt used, without this being essential.

Use is often made of hydrochloric acid, generally in the form of aqueous solutions having a weight for weight concentration of 10 to 20%.

In the present text, the expression aqueous solution used in the context of the process for the preparation of the catalysts also covers, except when otherwise mentioned, the above acidic aqueous solutions.

Mention may be made, as examples of soluble vanadium compounds, of vanadyl acetylacetonate, vanadyl trichloride, vanadium trifluoride, vanadium tetrafluoride, vanadium pentafluoride, vanadium tribromide, vanadium dichloride, vanadium trichloride, vanadium tetrachloride or vanadium triiodide.

Mention may be made, as examples of soluble antimony compounds, of antimony pentachloride, antimony trichloride, antimony tribromide, antimony trifluoride, antimony triiodide, antimony trioxide or stibine.

Mention may be made, as examples of soluble iron compounds, of iron dichloride, iron trichloride, iron dibromide, iron tribromide, iron diiodide, ferrous nitrate, ferrous sulphate, ferric sulphate, ferrous thiosulphate, ferric formate, ferric acetate, ferric acetylacetonate, ferric benzoate, ferric oleate, ferrous lactate or ferric lactate.

The saturated alcohols used in the process of the invention are more particularly alkanols and cycloalkanols. Use will preferably be made of alkanols and cycloalkanols in which the boiling point is not excessively high, in order to facilitate the operations of separation or of recycling by distillation or evaporation. Thus, alkanols having from 1 to 6 carbon atoms, such as methanol, ethanol, n-propanol, 2-propanol, n-butanol, 2-butanol, tert-butanol, pentanols and hexanols, and cyclohexanol are preferred.

The alcoholic solution or the aqueous solution obtained above is then mixed with an aqueous solution of an ammonium salt, so as to precipitate the mixed oxides. The operation is preferably carried out in an aqueous solution of an ammonium carboxylate (for example, acetate, citrate or tartrate), of ammonium oxalate, of ammonium carbonate or of ammonium hydrogenphosphate, which makes it possible to have a pH of between 5 and 9 and preferably in the region of 7. Thus, ammonium acetate at a concentration of two moles per liter in water has a pH in the region of 7.

In order to maintain the value of the pH of the solution preferably at a value in the region of 7, it may be necessary to progressively neutralize the acidity possibly formed during the precipitation of the mixed oxides (for example, hydrohalic acid formed when an antimony halide and/or an iron halide and/or a vanadium halide is/are used) or the possible acidity of the aqueous solution used, with the aid of a basic compound. It is preferable, in the process of the invention, to carry out this neutralization by controlled progressive addition of aqueous ammonia.

After precipitation of the mixed oxides of the invention, they are separated from the saturated alcohol/water or water liquid by any technique commonly used for this type of operation, in particular by filtration. The isolated mixed oxides are then dried, at atmospheric pressure or at reduced pressure, at a temperature lying, for example, between 30° C. and 200° C., without these values being of critical importance.

The mixed oxides of formula (I) are then calcined at a temperature of 400° C. to 800° C. The calcination is preferably carried out at a temperature of 500° C. to 750° C.

Preference is given, among the mixed oxides of formula (I) defined above, to those in which:

a represents a whole or fractional number equal to or less than 100 b represents a whole or fractional number equal to or less than 100 x represents a whole or fractional number determined by the oxidation state of the other elements.

Finally, preference is still more particularly given to the mixed oxides of formula (I) in which:

a represents a whole or fractional number from 0.5 to 50 b represents a whole or fractional number from 1 to 50 x represents a whole or fractional number determined by the oxidation state of the other elements.

Another subject of the present invention is a process for the ammoxidation of alkanes in the vapour phase in the presence of a solid catalyst containing at least one active phase, characterized in that the said active phase comprises at least one mixed oxide corresponding to the general empirical formula (I) and prepared according to the process defined above.

According to the present invention, alkanes having from 3 to 12 carbon atoms per molecule are reacted in the vapour phase with ammonia and oxygen in the presence of a catalyst whose active phase has just been indicated.

Of course, in the context of the present process, it is possible to use diluent gases which are inert under the reaction conditions, such as helium, nitrogen and argon. Likewise, steam can be added to the gaseous reaction mixture within wide limits. The reactive gas (alkane, ammonia, oxygen) can thus be diluted with an inert diluent and/or with steam. In this grouping, the content of steam can vary within wide limits, in particular from 0 to 50% and, preferably, between 3 and 30%. For a good implementation of the process according to the invention, the content of reactive gas will be at least 3% and preferably at least 20%.

Within the reactive gas, the respective volumie contents of alkane, ammonia and oxygen can vary within wide limits.

The alkane content in the reactive gas is preferably between 5 and 70%. The ammonia content is preferably between 3 and 50% and the oxygen content is preferably between 3 and 45%.

For a good implementation of the process according to the invention, the composition of the reactive mixture will preferably be chosen outside the explosive region.

Starting from propane, a mixture will be obtained containing essentially propylene and acrylonitrile. Acrylonitrile is an intermediate produced industrially on a large scale, propylene is a starting material traditionally used to produce acrylonitrile and various other intermediate products well known to those skilled in the art.

Starting from isobutane, a mixture will be obtained containing methacrylonitrile and isobutene or n-butenes.

The process according to the invention is more particularly suitable for the ammoxidation of propane.

If the alkane used can be of technical quality, it will not contain significant amounts of compounds containing ethylenic unsaturation. Thus, the propane involved will generally only contain trace amounts of propylene, for example less than 10%.

The process according to the invention is carried out in the form of a vapour phase reaction. Consequently, any device suitable for carrying out ammoxidation or oxidation reactions in the vapour phase can be used. The process can be carried out continuously or noncontinuously and it can comprise the use of a stationary bed or of a fluidized bed.

The reaction temperature is generally between 300° C. and 550° C. and, preferably, between 400° C. and 500° C.

The total pressure of the reaction mixture can be greater than or equal to atmospheric pressure. It is generally between 1 and 6 bar and, preferably, between 1 and 4 bar.

The gas flow rate is fixed such that the hourly volume rate is between 100 and 36,000 $h^{-1}$ and, preferably, between 200 and 20,000 $h^{-1}$.

The hourly volume rate is defined as the total gas volume/volume of the catalyst/hour ratio.

Of course, those skilled in the art will be able to find a compromise between the temperature, the gas flow rate, the precise nature of the catalyst used and the various other parameters of the reaction taking into account their production objectives.

The catalyst used in the process for the ammoxidation of alkanes can comprise solely one or a number of mixed vanadium, antimony and iron oxides defined above, constituting the active phase of the catalyst, or can additionally comprise an inorganic oxide, such as, for example, alumina, silica, silica/alumina, zirconia, cerite, magnesia, titanium oxide or niobium oxide, on which the said active phase is deposited or with which the active phase is mixed, by using various techniques known to those skilled in the art, such as impregnation or slurry deposition.

The catalytic phase, consisting of the active phase alone or of the active phase deposited on an inorganic oxide or mixed with the said inorganic oxide, can then be used in the bulk form or in the particulate state; it can therefore be used in the powder form or be shaped, for example as balls, pellets, extrudates or crushed particles, according to various known techniques.

For use of the process in a stationary bed, these techniques can be, for example, pelleting or coating on an inert substrate or on a ceramic or metal substrate of monolithic type.

For use of the process in a moving bed or in a fluidized bed, the catalytic phase is generally formed by atomization, drying and calcination.

The catalytic phases can, for example, be shaped by compression, so as to obtain pellets. These pellets can then optionally be crushed into fragments. The precise values of the pressure, diameter and thickness of the pellets and particle size of the fragments can be chosen by those skilled in the art according to the pressure drop acceptable in the reactor.

A variant of the preparation of the catalytic phase can consist in carrying out, in a single stage, the synthesis of the active phase and its deposition on an inorganic oxide or its mixture with the said inorganic oxide.

The catalytic phases can also be deposited on an inert support or can coat it. The nature of this support is not critical so long as it is chemically inert with respect to the reactants under the chosen reaction conditions. By way of examples of supports capable of being suitable for the preparation of catalysts which can be used in the context of the process according to the invention, there may be mentioned: silica, alumina, silica/alumina, sintered clay, carborundum, magnesia, magnesium silicate and diatomaceous earth. This support is preferably nonporous and can be especially based on refractory oxide in the particulate form, the most commonly employed support being clay-based. This support can, for example, consist of inert, complete, solid and rough clay balls with a diameter of between 0.5 and 6 mm. The precise value of the diameter of the balls can be chosen as a function of the acceptable pressure drop in the reactor. This support can also be made nonporous by enamelling.

This support can also be a ceramic substrate, the said substrate being preferably in the form of an inert and rigid structure of monolithic type comprising channels or ducts. Such supports are well known and have been widely described in the literature. The substrates used which are made of ceramic substance are especially those comprising, as the main substance, cordierite, alumina, mullite, porcelain, and the carbides of boron or silicon.

This substrate can also be a metal substrate. Such substrates are well known. Suitable metal substrates are in particular those obtained from iron, nickel and chromium alloys or those obtained from iron, chromium, aluminium and cobalt alloys, such as those known under the trade name Kanthal, or those obtained from iron, chromium, aluminium and yttrium alloys, known under the trade name Fecralloy. The metal can also be carbon steel or simple cast iron.

When a coated catalyst is resorted to, the amount of catalytic phase, which can vary within wide limits, is in practice between 1 and 50% and, preferably, between 5 and 35% by weight with respect to the support + catalytic phase combination.

Thus, certain catalysts, useful for an implementation of the process in a stationary bed, can be obtained by coating the crushed, intermediate or finished, catalytic phases in a way known per se. This conventional method consists in depositing a layer of intermediate or finished catalytic phase around inert but rough balls. Once the balls are covered with the desired quantity of the catalytic phase, they are dried with hot air between 70 and 150° C. for at least 30 minutes and then introduced into an oven in order to be calcined between 300 and 600° C., preferably between 450 and 500° C., for at least 3 hours.

Certain catalysts which are useful for an implementation of the process according to the invention in a moving bed or fluidized bed can be obtained by the technique, known per se, of drying by atomization in a preferably nonreducing atmosphere. By such an operation, followed if appropriate by calcination at a temperature of the order of 400 to 800° C., powders are obtained which are spherical in shape and have a diameter of between 5 and 700 $\mu$m.

Powders consisting of at least 80% by weight of particles whose sizes are between 5 and 200 $\mu$m are preferred in the context of use in a fluidized bed.

The catalytic phase, alone or thus used in the bulk form or in the particulate state, constitutes the catalyst.

The products of the reaction can be recovered from the effluent gases by any suitable means. For example, the effluent gases can pass into a condenser containing dilute sulphuric acid in order to neutralize the unreacted ammonia. The gases can then pass through a refrigerated absorbing column to condense the acrylonitrile, acetonitrile and hydrocyanic acid, the uncondensed vapours containing mainly unreacted propane, propylene, light hydrocarbons and, if appropriate, $CO_2$. The acrylonitrile and hydrocyanic acid can then be separated from the acetonitrile by distillation and the recovered acrylonitrile/hydrocyanic acid mixture can then be distilled in its turn to separate the acrylonitrile from the hydrocyanic acid.

The examples below illustrate the present invention.

EXAMPLES OF THE PREPARATION OF MIXED OXIDES

Example 1

Preparation of the Mixed Oxide (A) According to the Invention, of the Following Empirical Formula: $VSb_5Fe_{2.5}O_x$ A solution of 7.77 g of $FeCl_3 \cdot 6H_2O$, 3.05 g of vanadyl acetylacetonate and 17.22 g of $SbCl_5$ in 100 ml of an aqueous hydrochloric acid solution having a 15% weight for weight concentration is prepared.

The aqueous solution is poured dropwise into 500 ml of aqueous solution containing ammonium acetate (2 mol/liter) in order to have an initial pH of the order of 7.0. During the precipitation of the mixed V, Sb and Fe oxides, the pH, which tends to decrease due to the release of hydrochloric acid and the presence of hydrochloric acid in the aqueous solution, is kept constant by addition of a concentrated aqueous ammonia solution (containing 30% by weight).

The precipitate thus formed is isolated by filtration, washed with water, dried for 12 h at 140° C. and then calcined for 3 h at 700° C.

The compound of formula $VSb_5Fe_{2.5}O_x$ thus obtained is then compressed under a pressure of 4300 bars. Pellets with a diameter of 3 cm and with a thickness of approximately 0.5 cm are then obtained. These pellets are crushed into fragments with a particle size of between 0.3 and 0.8 cm, constituting the catalyst (A) in accordance with the invention.

Examples 2 to 7

Preparation of Different Mixed Oxides According to the Invention

Different mixed oxides are prepared by following the procedure described in Example 1 but by using different amounts of vanadyl acetylacetonate (Examples 2 and 5) or of antimony pentachloride and of ferric chloride (Examples 3, 4, 6 and 7).

The mixed oxides according to the invention exhibiting the following formulae are thus obtained:

Example 2 $VSb_{10}Fe_5O_x$ (reference B)
Example 3 $VSb_{12.5}Fe_5O_x$ (reference C)
Example 4 $VSb_{17.5}Fe_5O_x$ (reference D)
Example 5 $VSb_{20}Fe_{10}O_x$ (reference E)
Example 6 $VSb_{25}Fe_{10}O_x$ (reference F)
Example 7 $VSb_{30}Fe_{10}O_x$ (reference G)

Examples 8 and 9

Preparation of the Mixed Oxides (H) and (J) According to the Invention

A solution of 7.77 g of $FeCl_3 \cdot 6H_2O$, 1.52 g of vanadyl acetylacetonate and 21.4 g of $SbCl_5$ in 100 ml of absolute ethanol is prepared.

The ethanolic solution is poured dropwise into 500 ml of aqueous solution containing ammonium acetate (2 mol/liter) in order to have an initial pH of the order of 7.0. During the precipitation of the mixed V, Sb and Fe oxides, the pH, which tends to decrease due to the release of hydrochloric acid, is kept constant by addition of a concentrated aqueous ammonia solution (containing 30% by weight).

The precipitate thus formed is isolated by filtration, washed with water, dried for 12 h at 140° C. and then calcined for 3 h at 700° C.

The compound of formula $VSb_{12.5}Fe_5O_x$ thus obtained is then compressed under a pressure of 4300 bars. Pellets with a diameter of 3 cm and with a thickness of approximately 0.5 cm are then obtained. These pellets are crushed into fragments with a particle size of between 0.3 and 0.8 cm, constituting the catalyst (H) according to the invention.

A catalyst (J) according to the invention, with the composition $VSb_{20}Fe_{10}O_x$, is prepared according to the procedure used for the catalyst (H) but using different amounts of ferric chloride and of antimony pentachloride.

GENERAL PROCEDURE FOR THE AMMOXIDATION TESTS

The catalyst sample is brought beforehand to a temperature of 150° C. on a measuring bench while purging with helium for 10 min, and it is then subjected to a gas flow whose composition will be specified for each example and which contains propane, ammonia, oxygen, helium and, if appropriate, steam.

The total pressure of the reaction mixture, of between 1 and 6 bar, will also be specified for each example.

The total gas flow rate is defined so as to have an hourly volume rate (HVR) of between 100 and 36000 $h^{-1}$, the precise value of which will be indicated for each example.

Volume of active phase: 25 $cm^3$.

The principle of the ammoxidation test for propane is the following:

The catalyst is brought to a temperature $T_1$, for example 310° C., and, after stabilizing for 30 min at the temperature $T_1$, the composition of the mixture at the reactor outlet is determined by gas phase chromatography.

The conversion percentages and the selectivities obtained on the catalyst examined at the inlet temperature $T_1$ are calculated using relationships of the type:

conversion of propane (in mol %) = converted propane/introduced propane selectivity towards acrylonitrile (in mol %)=propane converted to acrylonitrile/converted propane.

The catalyst is then brought from 310 to 550° C. by increments of 20° C. and the conversion percentages and the selectivities are determined every 40 min.

In the ammoxidation examples below, the following conventions are used:

Temp = temperature of the reaction ct = contact time $DC(C_3H_8)$ = conversion of propane S(ACN) = selectivity towards acrylonitrile $S(ACN+C_3H_6)$ = selectivity towards acrylonitrile and propylene S(Ammox) = selectivitity towards acetonitrile, hydrocyanic acid and other ammoxidation by-products ACN Prod = acrylonitrile productivity expressed as g of acrylonitrile formed/liter of catalyst x hour.

The remainder to 100% of the selectivities corresponds to the formation of CO and $CO_2$ and optionally methane, ethane and ethylene.

EXAMPLES OF THE AMMOXIDATION OF PROPANE

Examples 10 to 20

Ammoxidation of propane is carried out, as described above, by using, as catalysts, active phases composed of the mixed oxides prepared according to the invention A, B, C, D, E, F, G, H and J.

The specific conditions used are the following:

hourly volume rate = 1800 $h^{-1}$ or 3600 $h^{-1}$ or 7200 $h^{-1}$ total pressure = 1.3 bar composition by volume of the reaction mixture: $C_3H_8$=25%

$NH_3$=10%

$O_2$=20%

He=45%

The temperature conditions and the results obtained are collected in Table 1 below.

TABLE 1

| Examples | Mixed oxide used | Temp (° C.) | ct | HVR ($h^{-1}$) | DC ($C_3H_8$) (in %) | S(ACN) (in %) | S(ACN + $C_3H_6$) (in %) | S(Ammox) (in %) | ACN Prod (g/l × h) |
|---|---|---|---|---|---|---|---|---|---|
| Example 10 | A | 365 | 2 s | 1800 | 12 | 17 | 40 | 21 | 20 |
|  |  | 385 |  |  | 24 | 17 | 33 | 13 | 40 |
|  |  | 405 |  |  | 27 | 16 | 37 | 14 | 43 |
|  |  | 425 |  |  | 29 | 18 | 41 | 14 | 52 |
| Example 11 | B | 390 | 2 s | 1800 | 10 | 27 | 35 | 31 | 27 |
|  |  | 415 |  |  | 29 | 26 | 31 | 11 | 75 |
|  |  | 430 |  |  | 29 | 34 | 39 | 10 | 98 |
|  |  | 445 |  |  | 29 | 35 | 41 | 8 | 101 |
| Example 12 | C | 410 | 2 s | 1800 | 15 | 35 | 39 | 14 | 52 |
|  |  | 430 |  |  | 16 | 46 | 49 | 11 | 73 |
| Example 13 | C | 410 | 1 s | 3600 | 9 | 47 | 51 | 18 | 84 |
|  |  | 430 |  |  | 12 | 49 | 53 | 13 | 117 |
| Example 14 | C | 410 | 0.5 s | 7200 | 3 | 53 | 68 | 21 | 63 |
|  |  | 430 |  |  | 7 | 54 | 62 | 25 | 150 |
|  |  | 450 |  |  | 11 | 60 | 69 | 17 | 262 |
|  |  | 470 |  |  | 15 | 53 | 58 | 12 | 316 |
| Example 15 | D | 410 | 2 s | 1800 | 5 | 41 | 50 | 23 | 20 |
|  |  | 430 |  |  | 6 | 43 | 50 | 16 | 26 |
|  |  | 450 |  |  | 8 | 48 | 55 | 13 | 38 |
|  |  | 470 |  |  | 11 | 51 | 59 | 8 | 56 |
| Example 16 | E | 410 | 2 s | 1800 | 8 | 35 | 42 | 12 | 28 |
|  |  | 430 |  |  | 10 | 39 | 45 | 10 | 39 |
|  |  | 450 |  |  | 18 | 44 | 49 | 8 | 79 |
|  |  | 470 |  |  | 26 | 40 | 44 | 7 | 103 |
| Example 17 | F | 410 | 2 s | 1800 | 4 | 42 | 46 | 35 | 17 |
|  |  | 430 |  |  | 8 | 49 | 52 | 21 | 39 |
|  |  | 450 |  |  | 12 | 50 | 53 | 14 | 60 |
|  |  | 470 |  |  | 15 | 47 | 49 | 12 | 70 |

TABLE 1-continued

| Examples | Mixed oxide used | Temp (° C.) | ct | HVR (h⁻¹) | DC (C₃H₈) (in %) | S(ACN) (in %) | S(ACN + C₃H₆) (in %) | S(Ammox) (in %) | ACN Prod (g/l × h) |
|---|---|---|---|---|---|---|---|---|---|
| Example 18 | G | 410 | 2 s | 1800 | 3 | 56 | 59 | 25 | 17 |
|  |  | 430 |  |  | 5 | 55 | 57 | 25 | 27 |
|  |  | 450 |  |  | 8 | 60 | 62 | 18 | 48 |
|  |  | 470 |  |  | 10 | 60 | 61 | 15 | 60 |
| Example 19 | H | 410 | 2 s | 1800 | 6 | 39 | 45 | 30 | 23 |
|  |  | 430 |  |  | 8 | 47 | 52 | 23 | 37 |
|  |  | 450 |  |  | 13 | 49 | 54 | 16 | 63 |
|  |  | 470 |  |  | 15 | 48 | 53 | 12 | 71 |
| Example 20 | J | 410 | 2 s | 1800 | 6 | 33 | 40 | 24 | 20 |
|  |  | 430 |  |  | 9 | 40 | 44 | 20 | 36 |
|  |  | 450 |  |  | 14 | 49 | 53 | 13 | 68 |
|  |  | 470 |  |  | 20 | 46 | 49 | 8 | 91 |

What is claimed is:

1. Process for the preparation of a mixed oxide containing vanadium, antimony and iron corresponding to the general empirical formula (I):

$$VSb_aFe_bO_x \quad (I)$$

in which:
 a represents a whole or fractional number equal to or greater than 0.1
 b represents a whole or fractional number equal to or greater than 0.5
 x represents a whole or fractional number determined by the oxidation state of the other elements,
comprising:
 dissolving respective vanadium, antimony and iron compounds in at least one saturated alcohol,
 bringing the alcoholic solution thus obtained into contact with an aqueous solution containing an ammonium salt, in order to precipitate the mixed oxide, and
 separating and calcining the mixed oxide thereby obtained.

2. Process according to claim 1, wherein the soluble vanadium compound is vanadyl acetylacetonate, vanadyl trifluoride, vanadium trifluoride, vanadium tetrafluoride, vanadium pentafluoride, vanadium tribromide, vanadium dichloride, vanadium trichloride, vanadium tetrachloride or vanadium triiodide.

3. Process according to claim 1, wherein the soluble antimony compound is antimony pentachloride, antimony trichloride, antimony tribromide, antimony trifluoride, antimony triiodide, antimony trioxide or stibine.

4. Process according to claim 1, wherein the soluble iron compound is iron dichloride, iron trichloride, iron dibromide, iron tribromide, iron diiodide, ferrous nitrate, ferrous sulphate, ferric sulphate, ferrous thiosulphate, ferric formate, ferric acetate, ferric acetylacetonate, ferric benzoate, ferric oleate, ferrous lactate or ferric lactate.

5. Process according to claim 1, wherein the saturated alcohols used are alkanols and cycloalkanols.

6. Process according to claim 1, wherein the alcoholic solution obtained is mixed with an aqueous solution of an ammonium salt to precipitate the mixed oxides and to obtain a final solution having a pH of between 5 and 9.

7. Process according to claim 6, wherein the value of the pH of the final solution is maintained at about 7 by progressively neutralizing acidity formed with a basic compound.

8. Process according to claim 1, further comprising calcining the mixed oxides at a temperature of 400° C. to 800° C.

9. Process according to claim 1, wherein it is applied to the preparation of mixed oxides of general formula (I) wherein:
 a represents a whole or fractional number equal to or less than 100
 b represents a whole or fractional number equal to or less than 100 and
 x represents a whole or fractional number determined by the oxidation state of the other elements.

10. Process for the ammoxidation of alkanes in the vapour phase in the presence of a solid catalyst containing at least one active phase, wherein said active phase comprises at least one mixed oxide corresponding to the general empirical formula (I) and prepared according to the process of claim 1.

11. Process according to claim 10, wherein alkanes having from 3 to 12 carbon atoms per molecule are reacted in the vapour phase with ammonia and oxygen.

12. Process according to claim 10, wherein the reactive gas comprises alkane, ammonia and oxygen.

13. Process according to claim 10, wherein the reaction temperature is between 300° C. and 550° C.

14. Process for the preparation of a mixed oxide containing vanadium, antimony and iron corresponding to the general empirical formula (I):

$$VSb_aFe_bO_x \quad (I)$$

in which:
 a represents a whole or fractional number equal to or greater than 0.1
 b represents a whole or fractional number equal to or greater than 0.5
 x represents a whole or fractional number determined by the oxidation state of the other elements,
comprising:
 dissolving respective vanadium, antimony and iron compounds in an acidic aqueous solution having a pH of less than or equal to 2,
 bringing the aqueous solution thus obtained into contact with an aqueous solution containing an ammonium salt, in order to precipitate the mixed oxide, and
 separating and calcining the mixed oxide thereby obtained.

15. Process according to claim 14, wherein the acid used to prepare the acidic aqueous solution is any strong inorganic or organic acid capable of giving a solution having a pH of less than or equal to 2.

16. Process according to claim 14, wherein the acid used to prepare the acidic aqueous solution is hydrochloric, hydrobromic, sulphuric, nitric or trifluoroacetic acids.

17. Process according to claim 14, wherein the soluble vanadium compound is vanadyl acetylacetonate, vanadyl trichloride, vanadium trifluoride, vanadium tetrafluoride, vanadium pentafluoride, vanadium tribromide, vanadium dichloride, vanadium trichloride, vanadium tetrachloride or vanadium triiodide.

18. Process according to claim 14, wherein the soluble antimony compound is antimony pentachloride, antimony trichloride, antimony tribromide, antimony trifluoride, antimony triiodide, antimony trioxide or stibine.

19. Process according to claim 14, wherein the soluble iron compound is iron dichloride, iron trichloride, iron dibromide, iron tribromide, iron diiodide, ferrous nitrate, ferrous sulphate, ferric sulphate, ferrous thiosulphate, ferric formate, ferric acetate, ferric acetylacetonate, ferric benzoate, ferric oleate, ferrous lactate or ferric lactate.

20. Process according to claim 14, wherein the acidic aqueous solution obtained is mixed with an aqueous solution of an ammonium salt to precipitate the mixed oxides and obtain a final solution having a pH of between 5 and 9.

21. Process according to claim 20, wherein the value of the pH of the final solution is maintained at about 7 by progressively neutralizing acidity formed with a basic compound.

22. Process according to claim 14, further comprising calcining the mixed oxides at a temperature of 400° C. to 800° C.

23. Process according to claim 14, wherein it is applied to the preparation of mixed oxides of general formula (I) wherein:

a represents a whole or fractional number equal to or less than 100 b represents a whole or fractional number equal to or less than 100 and x represents a whole or fractional number determined by the oxidation state of the other elements.

24. Process for the ammoxidation of alkanes in the vapour phase in the presence of a solid catalyst containing at least one active phase, wherein said active phase comprises at least one mixed oxide corresponding to the general empirical formula (I) and prepared according to the process of claim 14.

25. Process according to claim 24, wherein alkanes having from 3 to 12 carbon atoms per molecule are reacted in the vapour phase with ammonia and oxygen.

26. Process according to claim 24, wherein the reactive gas comprises alkane, ammonia and oxygen.

27. Process according to claim 24, wherein the reaction temperature is between 300° C. and 550° C.

* * * * *